(12) United States Patent
Wiener et al.

(10) Patent No.: US 6,678,621 B2
(45) Date of Patent: Jan. 13, 2004

(54) OUTPUT DISPLACEMENT CONTROL USING PHASE MARGIN IN AN ULTRASONIC SURGICAL HAND PIECE

(75) Inventors: Eitan T. Wiener, Cincinnati, OH (US); Foster Stulen, Mason, OH (US); Ashvani K. Madan, Mason, OH (US); Kenneth S. Kramer, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 355 days.

(21) Appl. No.: 09/827,575

(22) Filed: Apr. 6, 2001

(65) Prior Publication Data

US 2002/0165680 A1 Nov. 7, 2002

Related U.S. Application Data

(60) Provisional application No. 60/242,105, filed on Oct. 20, 2000.

(51) Int. Cl.[7] .................. G01R 23/00; A61B 17/32
(52) U.S. Cl. .................................. 702/75; 606/178
(58) Field of Search .......................... 702/75, 64, 65, 702/106; 606/167, 169, 178

(56) References Cited

U.S. PATENT DOCUMENTS

| | | | |
|---|---|---|---|
| 2,917,691 A | 12/1959 | De Prisco et al. | 318/118 |
| 5,001,649 A | 3/1991 | Lo et al. | 702/124 |
| 5,026,387 A | 6/1991 | Thomas | 606/169 |
| 5,112,300 A | 5/1992 | Ureche | 604/22 |
| 5,180,363 A | 1/1993 | Idemoto et al. | 604/22 |
| 5,400,267 A | 3/1995 | Denen et al. | 702/59 |
| 5,425,704 A | 6/1995 | Sakurai et al. | 604/22 |
| 5,449,370 A | 9/1995 | Vaitekunas | 606/169 |
| 5,630,420 A | 5/1997 | Vaitekunas | 600/459 |
| 5,707,369 A | 1/1998 | Vaitekunas et al. | 606/31 |
| 5,728,130 A | 3/1998 | Ishikawa et al. | 606/185 |
| 5,879,364 A | 3/1999 | Bromfield et al. | 606/169 |
| 5,968,007 A | 10/1999 | Simon et al. | 604/22 |
| 6,017,354 A | 1/2000 | Culp et al. | 606/170 |
| 6,019,775 A | 2/2000 | Sakurai | 606/169 |
| 6,066,135 A | 5/2000 | Honda | 606/39 |
| 6,090,123 A | 7/2000 | Culp et al. | 606/180 |
| 6,480,796 B2 * | 11/2002 | Wiener | 702/106 |
| 6,537,291 B2 * | 3/2003 | Friedman et al. | 606/169 |
| 2002/0049427 A1 * | 4/2002 | Wiener et al. | 606/1 |
| 2002/0049462 A1 * | 4/2002 | Friedman et al. | 606/169 |
| 2002/0049552 A1 * | 4/2002 | Wiener et al. | 702/72 |
| 2002/0052616 A1 * | 5/2002 | Wiener et al. | 606/169 |
| 2002/0062132 A1 * | 5/2002 | Kramer et al. | 606/169 |
| 2002/0077645 A1 * | 6/2002 | Wiener et al. | 606/169 |
| 2002/0161385 A1 * | 10/2002 | Wiener et al. | 606/169 |

FOREIGN PATENT DOCUMENTS

| | | | |
|---|---|---|---|
| EP | 1 025 806 A1 | | 8/2000 |
| EP | 1 199 044 | * | 4/2002 |

* cited by examiner

*Primary Examiner*—Michael Nghiem (57) ABSTRACT

An ultrasonic surgical hand piece is caused to be driven with an output displacement that is correlated with the phase margin, which is the difference of the resonant frequency and the anti-resonant frequency of the hand piece. A frequency sweep is conducted to find the resonant frequency and the anti-resonant frequency for the hand piece. The resonant frequency is measured at a point during the frequency sweep where the impedance of the hand piece is at its minimum. The anti-resonant frequency is measured at a point during the frequency sweep where the impedance of the hand piece is at its maximum. Using a target or specific output displacement, a drive current is calculated based on the phase margin which is the difference between the resonant frequency and the anti-resonant frequency. The hand piece is caused to be driven with the output displacement, by accordingly controlling the current output from a generator console for driving the hand piece.

20 Claims, 7 Drawing Sheets

| $F_r$ (Hz) | $F_a$ (Hz) | Phase margin (Hz) | Displacement (μM) |
|---|---|---|---|
| 55499 | 55734 | 235 | 20.521 |
| 55477 | 55717 | 240 | 20.292 |
| 55480 | 55712 | 232 | 20.514 |
| 55477 | 55714 | 237 | 20.356 |
| 55482 | 55725 | 243 | 20.187 |
| 55452 | 55697 | 245 | 19.775 |
| 55452 | 55709 | 257 | 19.056 |
| 55489 | 55742 | 253 | 18.717 |
| 55465 | 55722 | 257 | 18.834 |

FIG. 6

OUTPUT DISPLACEMENT CONTROL USING PHASE MARGIN IN AN ULTRASONIC SURGICAL HAND PIECE

RELATED APPLICATIONS

The present invention relates to, and claims priority of, U.S. Provisional Patent Application Ser. No. 60/242,105 filed on Oct. 20, 2000, having the same title as the present invention, which is incorporated herein by reference.

BACKGROUND OF THE INVENTION

1. Field of the Invention

The present invention generally relates to ultrasonic surgical systems and more particularly, to controlling the output displacement of an ultrasonic surgical hand piece based on the "phase margin" which is the difference between the resonant frequency and the anti-resonant frequency.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering, which increases the risk of spreading infectious diseases to operating room personnel. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop that includes a voltage controlled oscillator, a frequency divider, a power switch, a match net and a phase detector, stabilizes the frequency applied to the hand piece. A microprocessor controls the amount of power by sampling the frequency current and voltage applied to the hand piece, because these parameters change with load on the blade.

The power versus load curve in a generator in a typical ultrasonic surgical system, such as that described in the Thomas patent has two segments. The first segment has a positive slope of increasing power, as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, keeps monitoring of the transducer current to voltage phase angle and maintains the transducer resonating by driving it at the resonance frequency. A key function of such systems is to maintain the transducer resonating across load and temperature changes that vary the resonance frequency.

The prior art ultrasonic generator systems have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Moreover, using different handpieces with an ultrasonic surgical system could lead to performance problems. Different hand pieces of similar design have variations of output displacement within a certain ragne of input current to the hand piece. Excessive or improper displacement can result in the discarding of hand pieces due to poor performance or damaged blades.

Further, over time, hand piece performance can vary due to aging, environmental exposure, number of uses and the like.

Therefore, there is a general need in the art for an improved system and method for controlling the output displacement in an ultrasonic surgical hand piece which overcomes these and other disadvantages in the prior art.

SUMMARY OF THE INVENTION

The correlation of phase margin with output displacement of an ultrasonic hand piece is used to set the output current for a specific hand pieces to achieve desired hand piece displacement.

In an illustrative embodiment of the invention, a frequency sweep is conducted to find the resonant frequency and the anti-resonant frequency for the hand piece. The resonant frequency is measured at a point during the frequency sweep where the impedance of the hand piece is at its minimum. The anti-resonant frequency is measured at a point during the frequency sweep where the impedance of the hand piece is at its maximum. The phase margin, which is the difference between the resonant frequency and the anti-resonant frequency, is calculated. Using a target or specific output displacement, a drive current is calculated based on the phase margin which is stored in the hand piece. The hand piece is caused to be driven so as to maintain this displacement by accordingly controlling the current output from the generator console for driving the hand piece.

According to a further embodiment of the invention, the hand piece and the ultrasonic generator are caused to go through a calibration process for setting the drive current based on the correlation of the phase margin with the output displacement. During the calibration process, a frequency sweep is conducted to find the resonant frequency and the anti-resonant frequency for the hand piece. The phase margin is then calculated. Using a target or specific output displacement, a drive current is calculated based on the phase margin which is stored in the hand piece. During operation of the hand piece, the memory in the hand piece is accessed and a particular drive current for driving the hand piece is selected based on the correlation of the output displacement with the phase margin. The hand piece is caused to be driven with the output displacement, by accordingly controlling the current output from the generator console for driving the hand piece.

BRIEF DESCRIPTION OF THE DRAWINGS

The foregoing and other advantages and features of the invention will become more apparent from the detailed description of the preferred embodiments of the invention given below with reference to the accompanying drawings (not necessarily drawn to scale) in which.

DETAILED DESCRIPTION OF THE PREFERRED EMBODIMENTS

Figure 1:
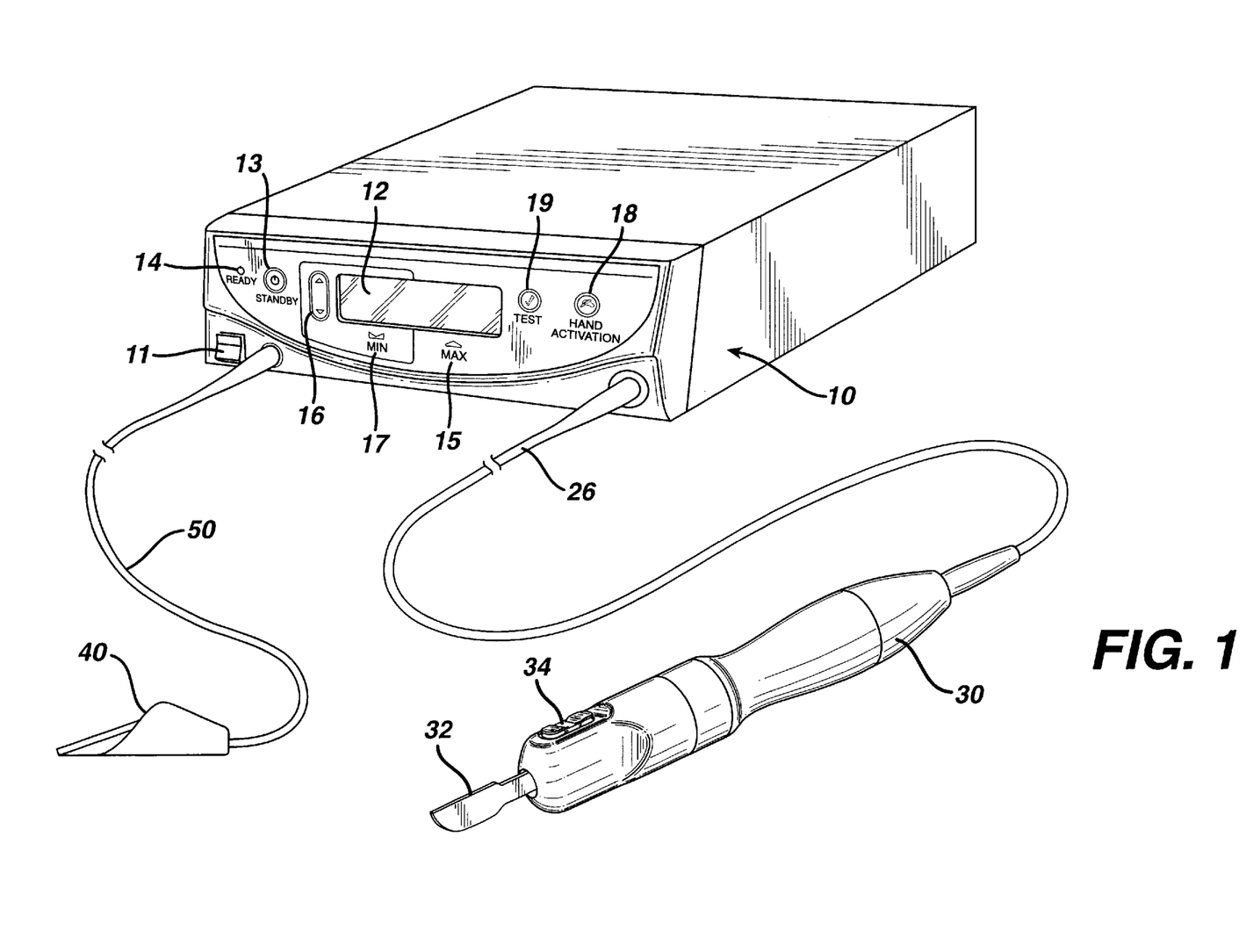
FIG. 1 is an illustration of a console for an ultrasonic surgical cutting and hemostasis system, as well as a hand piece and foot switch in which the method of the present invention is implemented.

FIG. 1 is an illustration of a system for implementing surgical procedures according to the invention. By means of a first set of wires in cable 26, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 26. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means, such as, percentage of maximum cutting power, or numerical power levels associated with cutting power. The liquid crystal display device 12 can also be utilized to display other parameters of the system. Power switch 11 is used to turn on the unit. Power up tests are performed. When power up tests and initialization are complete the "standby" light 13 is illuminated. If the unit is supplying maximum power, the MAX light 15 is illuminated. If a power level less than maximum is being delivered, the MIN light 17 is illuminated. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 2:
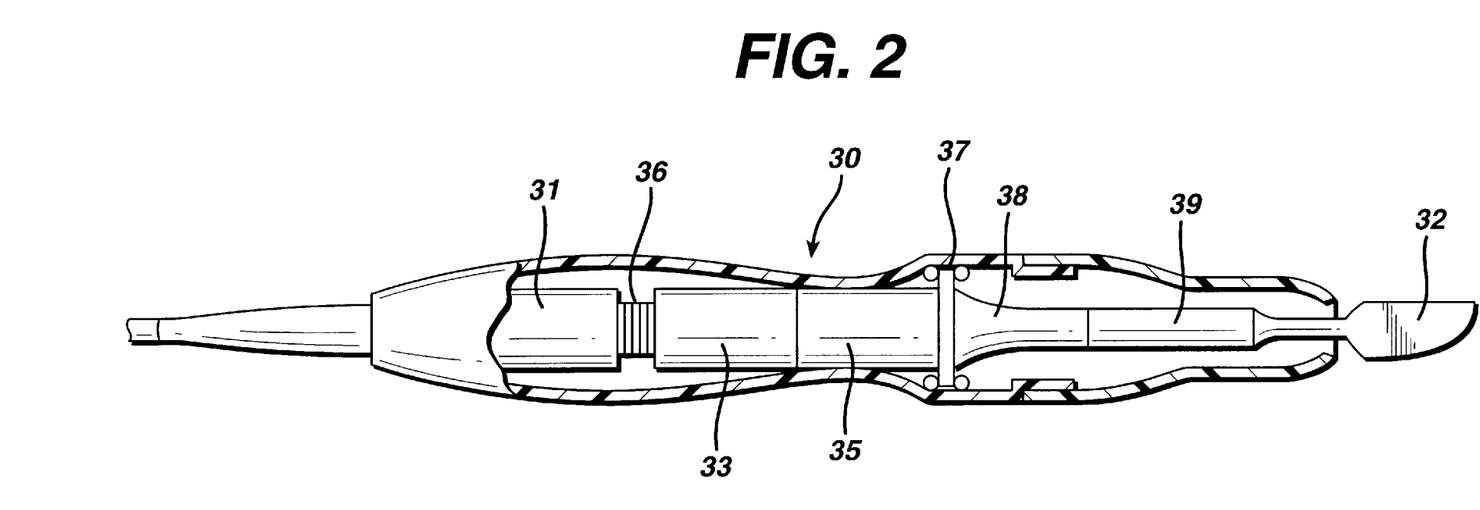
FIG. 2 is a schematic view of a cross section through the ultrasonic scalpel hand piece of the system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a blade coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node when the transducer is driven with a current of about 380 mA RMS at the transducers' resonant frequency. However, the current providing the maximum motion will vary with each hand piece and is a value stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade coupler 39 are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into blade movement of about 40 to 100 microns.

Figure 3A:
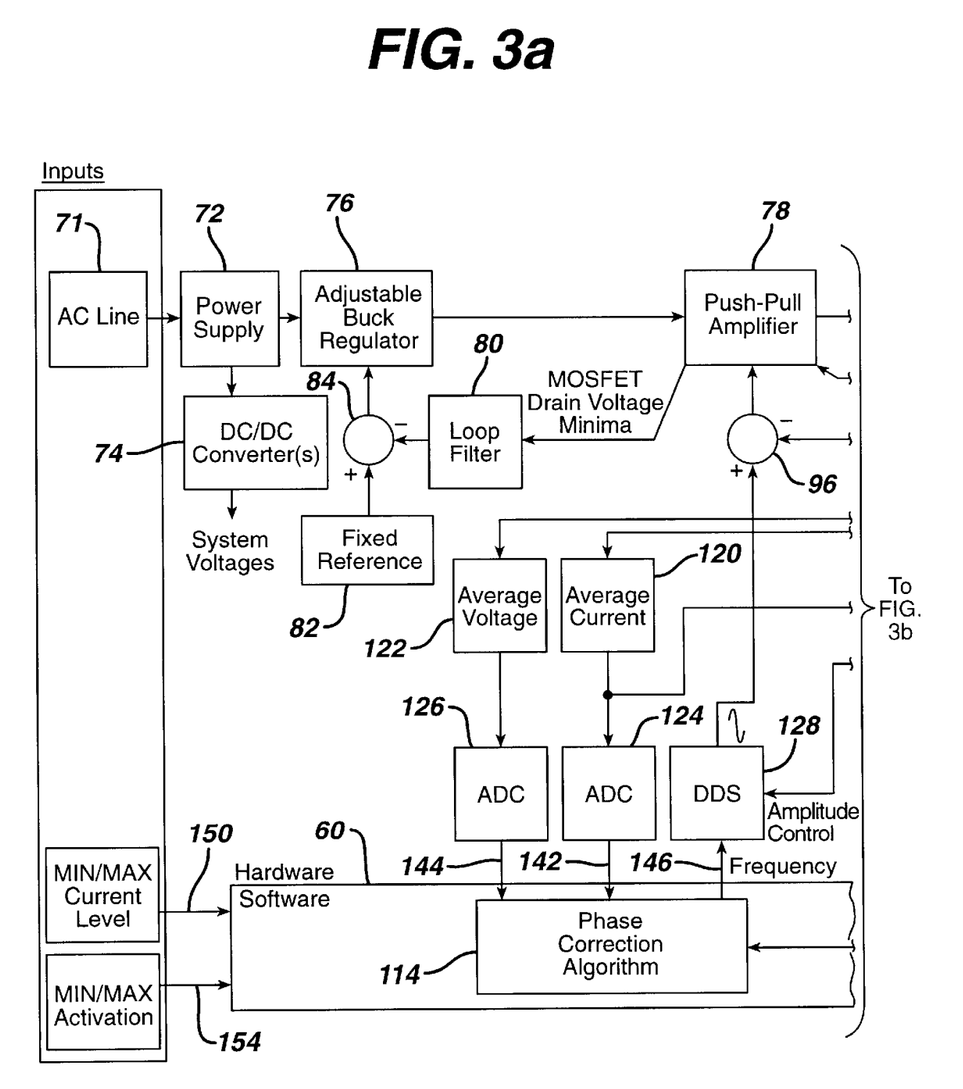
FIG. 3A and FIG. 3B are block diagrams illustrating the ultrasonic console according to an embodiment of the invention.
Figure 3B:
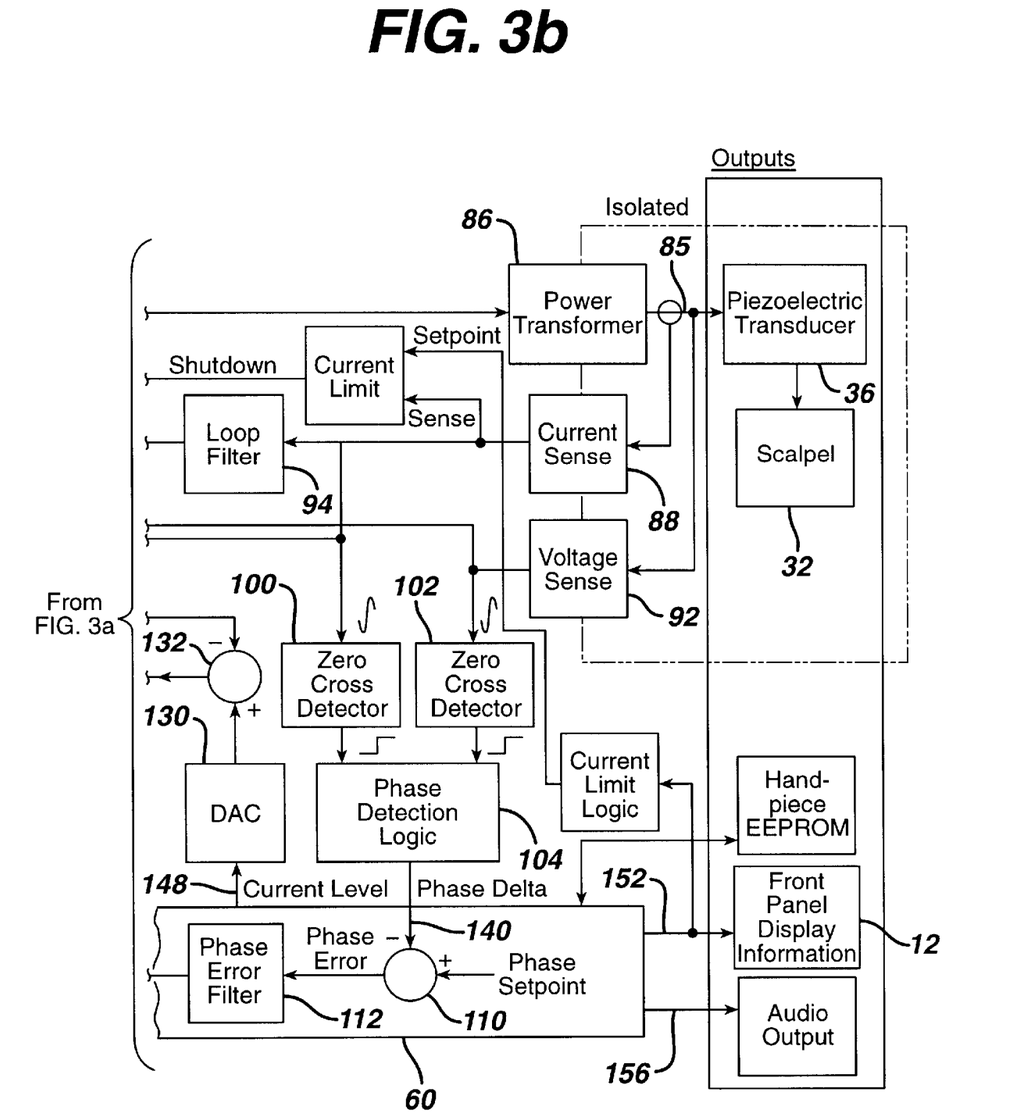

The system which creates the ultrasonic electrical signal for driving the transducer in the hand piece is illustrated in FIG. 3A and FIG. 3B. This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 600 kHz, to find resonance. Also, the system can sweep up from 50 kHz and hop over 51 kHz where the undesired resonance is located. In any event, the system has a great degree of flexibility.

In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3B) to the console front panel display 12.

To actually cause the surgical blade to vibrate, the user activates the foot switch 40 or the hand piece switch 34. This activation puts a signal on line 85 in FIG. 3B. This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

As described herein with respect to FIG. 2, FIG. 3A and FIG. 3B and in the related U.S. application Ser. No. 09/693,621 and incorporated herein by reference, the parts of the hand piece 30 in operational mode are designed, as a whole, to oscillate at generally the same resonant frequency, where the elements of the hand piece 30 are tuned so that the resulting length of each such element is one-half wavelength or a multiple thereof. Microprocessor or DSP 60, using a phase correction algorithm, controls the frequency at which the parts of the hand piece 30 oscillate. Upon activation of the hand piece 30, the oscillating frequency is set at a startup value or nominal resonant frequency such as 50 kHz which is stored in memory. A sweep of a frequency range between a start sweep point and a stop sweep point is effected under the control of the DSP 60 until the detection of a change in impedance which indicates the approach to the resonant frequency. The change in impedance refers to the impedance of the hand piece and any attached blade, which maybe modeled by a parallel equivalent circuit for mathematically modeling the algorithm for controlling the operation of the hand piece 30 as described in the related U.S. application Ser. No. 09/693,621. The resonant frequency is the frequency at a point during the frequency sweep where the impedance of the equivalent circuit is at its minimum and the anti-resonant frequency is the frequency where the impedance is maximum. Phase margin is the difference between the resonant frequency and an anti-resonant frequency. A correlation between the phase margin and the output displacement of the hand piece 30 exists which can advantageously be used to control the displacement so that the hand piece 30 operates at its optimal performance level.

In order to obtain the impedance measurements and phase measurements, the DSP 60 and the other circuit elements of FIGS. 3A and 3B are used. In particular, push-pull amplifier 78 delivers the ultrasonic signal to a power transformer 86, which in turn delivers the signal over a line 85 in cable 26 to the piezoelectric transducers 36 in the hand piece. The current in line 85 and the voltage on that line are detected by current sense circuit 88 and voltage sense circuit 92. The voltage and current sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 140, which represents the difference in phase between the current and voltage. The size of this phase difference is also an indication of how close the system is operating to the resonant frequency. These signals can be used as part of a phase lock loop that cause the generator frequency to lock onto resonance, e.g., by comparing the phase delta to a phase set point in the DSP in order to generate a frequency signal to a direct digital synthesis (DDS) circuit 128 that drives the push-pull amplifier 78.

Further, the impedance and phase values can be used as indicated above in a diagnosis phase of operation to detect if the blade is loose. In such a case the DSP does not seek to establish phase lock at resonance, but rather drives the hand piece at particular frequencies and measures the impedance and phase to determine if the blade is tight.

Figure 4:
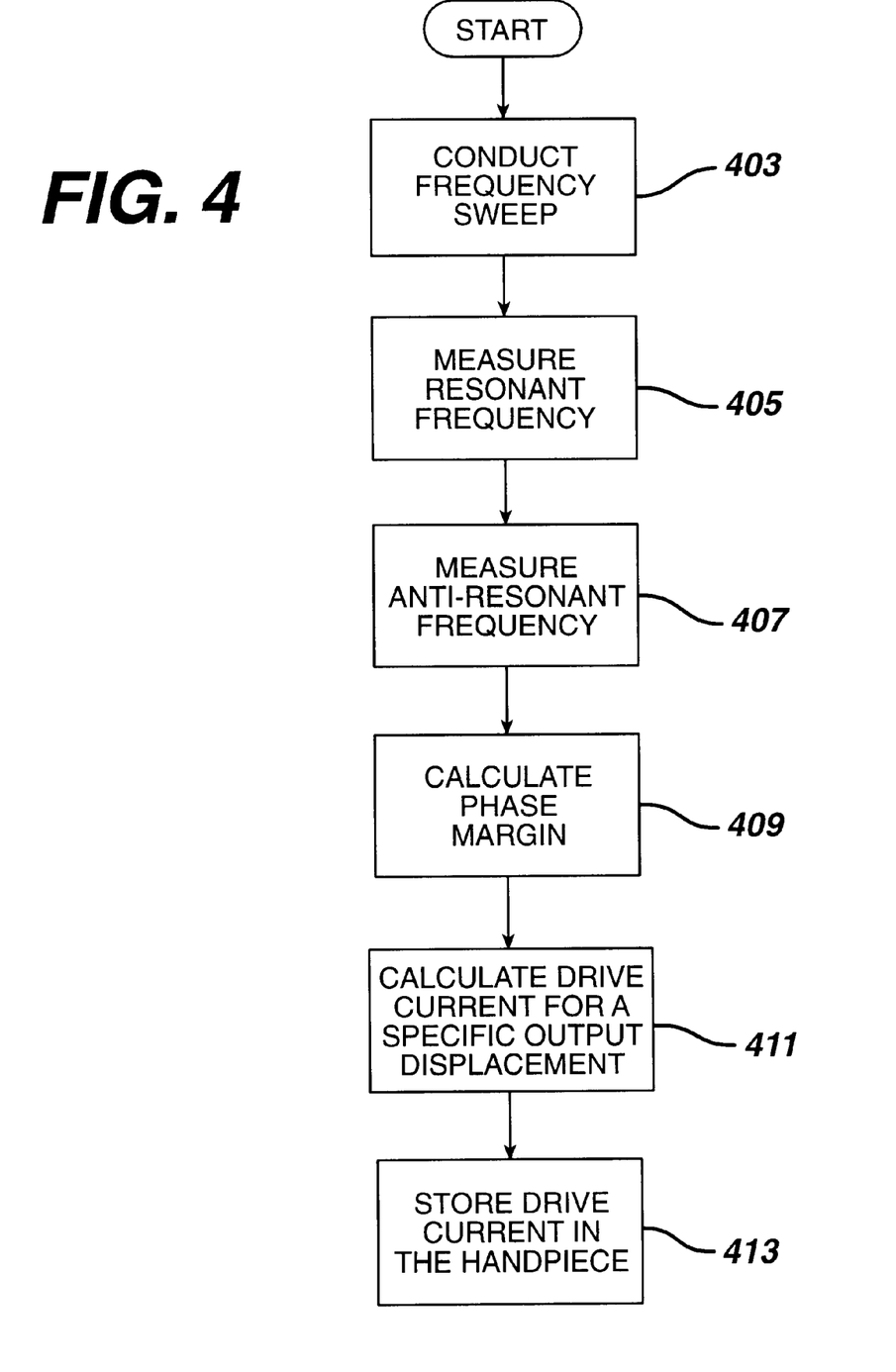
FIG. 4 is a flow diagram generally illustrating the method according to the invention for determining the drive current of the ultrasonic surgical hand piece based on phase margin.

FIG. 4 is a flow diagram that generally illustrates the method according to the invention for determining the drive current of the ultrasonic surgical hand piece based on phase margin. A frequency sweep is conducted in the hand piece 30 to find the resonant frequency and the anti-resonant frequency for the hand piece 30 (step 403). The resonant frequency is measured at a point during the frequency sweep where the impedance of the hand piece 30 is at its minimum (step 405). The anti-resonant frequency is measured at a point during the frequency sweep where the impedance of the hand piece 30 is at its maximum (step 407). In step 409, the phase margin is calculated which is the difference between the resonant frequency and the anti-resonant frequency. Using a target or specific output displacement, a drive current is calculated based on the phase margin (step 411). In step 413, the drive current is stored in the hand piece 30. The hand piece 30 is driven to maintain the output displacement, by accordingly controlling the current output from console 10. The method of FIG. 4 may also be performed with a known blade attached.

An embodiment of the method according to the invention can be implemented while the hand piece is being manufactured at the factory. The phase margin for a newly build hand piece is measured using an impedance analyzer (such as an HP 4192A commercially available from Hewlett Packard™). The impedance analyzer is programmed to find the resonant and anti-resonant frequencies for calculation of the phase margin. This data is transferred to a personal computer (PC) connected therewith which uses the phase margin to calculate a drive current for driving the hand piece which produces the desired displacement on the hand piece (e.g., 22 microns). The hand piece contains a memory, e.g., an EEPROM. The hand piece is connected to the PC's serial port through an interface which mates with the hand piece connector. The PC downloads the value of the drive current computed based on the phase margin calculation to a specified memory location in the EEPROM. During operation, the generator console uses this drive current value to control the generator current output to the hand piece.

Figure 5:
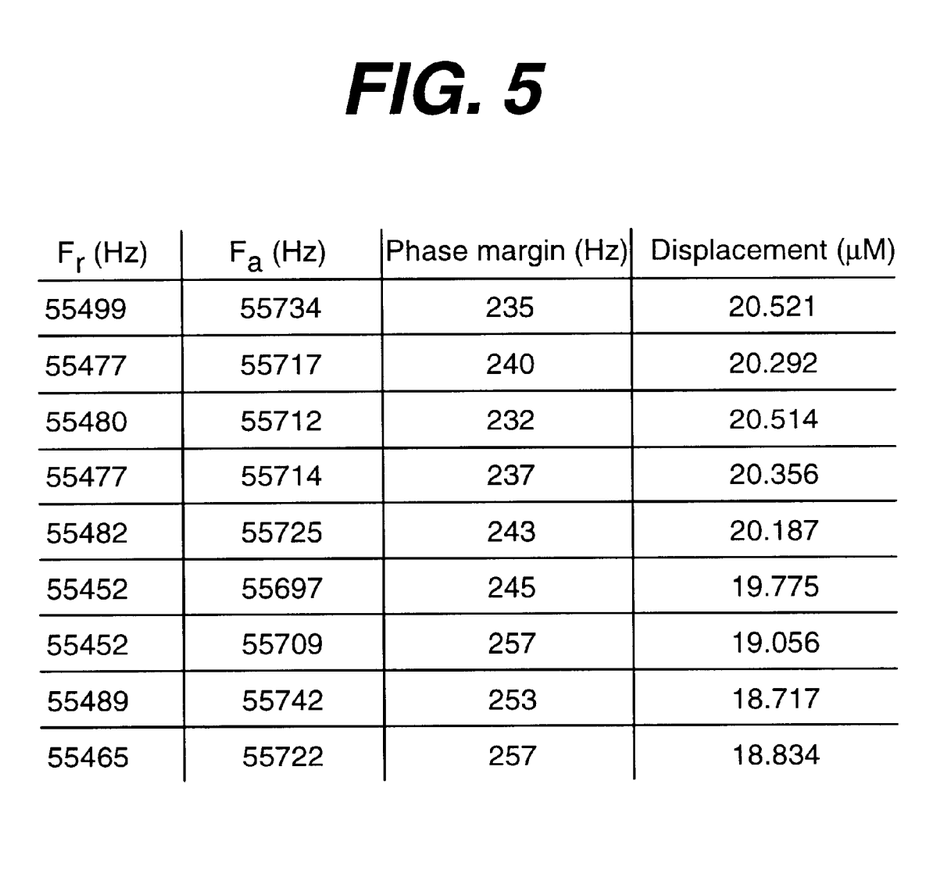
FIG. 5 is an exemplary tabulation of the correlation between the phase margin and displacement for a particular output drive current of an ultrasonic surgical hand piece according to the invention.

FIG. 5 is an exemplary tabulation of the correlation between the phase margin and displacement for a particular output drive current of an ultrasonic surgical hand piece according to the invention. The data in the tabulation can be stored in memory (in either test equipment for the hand piece at a factory during manufacture, or a generator console for the hand piece in the field). It includes data for the resonant frequency (the first column $F_r$), the anti-resonant frequency (the second column $F_a$), the phase margin which is the difference of the resonant frequency and the anti-resonant frequency (the third column), and the output displacement of the hand piece 30 in microns for a specific drive current (the fourth column). During actual operation, the tabulation stored in memory is accessed and console 10 drives the hand piece 30 with a calculated drive current to achieved desired displacement as will be described below.

In a specific embodiment according to the invention, the correlation of the phase margin and the output displacement for driving the hand piece 30 is empirically found to be:

$$\text{Displacement} = 38.156 - 0.0751 \times \text{Phase Margin} \quad (\text{Eq. 1})$$

This particular correlation can also be stored in memory in console 10. The resonant frequency and the anti-resonant frequency are measured. Console 10 drives the hand piece with the output displacement correlated with the phase margin measured for that particular hand piece based on the calculation according to the correlation in Eq. 1.

Equivalently to Equation 1, the terms can be rearranged to calculate how much current is needed to drive a particular hand piece to a desired displacement. Given that a transducer running in tune at the resonance point, current is proportional to displacement, e.g.

$$I \alpha D \quad (\text{Eq.2})$$

then the relationship between a measured displacement and a desired displacement is:

$$\frac{D \text{ measured}}{D \text{ desired}} = \frac{I \text{ measured}}{I \text{ desired}} \quad (\text{Eq. 3})$$

therefore so $$I \text{ desired} = \frac{D \text{ desired } I \text{ measured}}{D \text{ measured}} \quad (\text{Eq. 5})$$

Thus, if it is convenient to store the desired current needed to drive a particular hand piece to a desired displacement, Equations 1 and 5 can be used to solve for an I desired value for a given hand piece.

Figure 6:
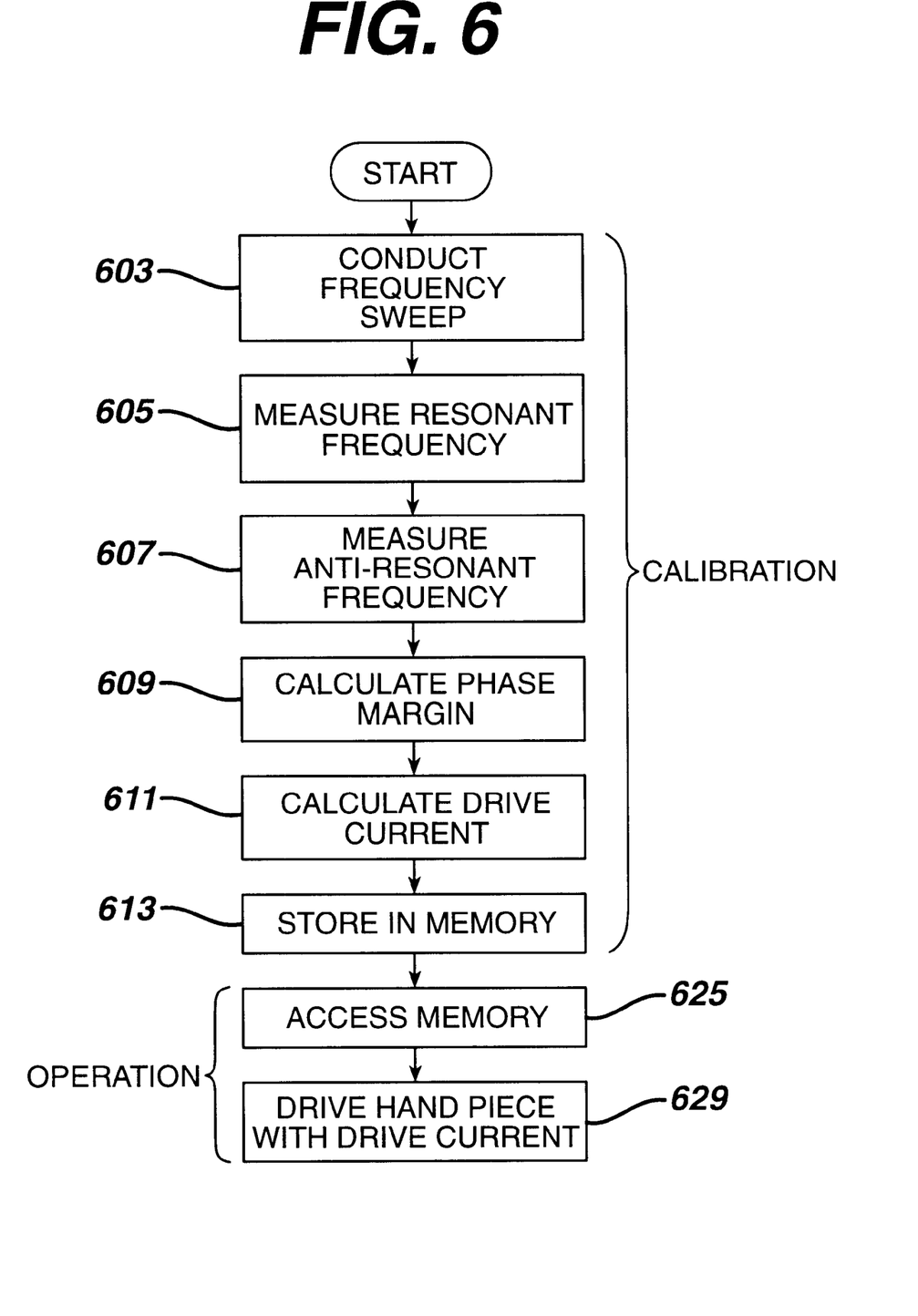
FIG. 6 is a flow diagram that illustrates an exemplary calibration and operation of the ultrasonic surgical hand piece according to a further embodiment of the invention.

According to a further embodiment of the invention, the hand piece 30 and console 10 are caused to go through a calibration process for correlating the phase margin with the output displacement. The calibration process is particularly useful for hand piece calibration after the hand piece has been in use in the field for a period of time which may result in a drift or downgrade of hand piece performance. FIG. 6 is a flow diagram illustrating an exemplary calibration and operation of the ultrasonic surgical hand piece according to the invention. A calibration process is implemented. In particular, a frequency sweep is conducted to find the resonant frequency and the anti-resonant frequency for the hand piece 30 (step 603). The resonant frequency is measured at a point during the frequency sweep where the impedance of the hand piece 30 is at its minimum (step 605). The anti-resonant frequency is measured at a point during the frequency sweep where the impedance of the hand piece 30 is at its maximum (step 607). In step 609, the phase margin is calculated, which is the difference between the resonant frequency and the anti-resonant frequency. The drive current is calculated based on the phase margin (step 611). In step 613, the drive current stored in memory in the hand piece 30 (such as in an EEPROM in the hand piece 30).

During normal operation of the hand piece 30, the memory is accessed (step 625), and a particular drive current for driving the hand piece 30 is selected based on the correlation of the phase margin with the output displacement. In step 629, the hand piece 30 is caused to be driven with the drive current signal, by accordingly controlling the current output from console 10 for driving the hand piece 30.

It is contemplated that other correlations between displacement and hand piece model parameters can be used to control displacement. Phase-margin using the parallel transducer model includes Co, Cs, Rs, and Ls. Correlations between any model parameter and displacement may be used for control.

Although the invention has been particularly shown and described in detail with reference to the preferred embodiments thereof, the embodiments are not intended to be exhaustive or to limit the invention to the precise forms disclosed herein. It will be understood by those skilled in the art that many modifications in form and detail may be made without departing from the spirit and scope of the invention. Similarly, any process steps described herein may be interchangeable with other steps to achieve substantially the same result. All such modifications are intended to be encompassed within the scope of the invention, which is defined by the following claims and their equivalents.

We claim:

1. A method for operating an ultrasonic surgical hand piece comprising the steps of:
    measuring a resonant frequency of the hand piece;
    measuring an anti-resonant frequency of the hand piece;
    calculating a phase margin which is the difference of the resonant frequency and the anti-resonant frequency;
    correlating the phase margin with an output displacement;
    calculating a drive current based on the correlation of the phase margin with the output displacement; and
    driving the hand piece with the drive current.

2. The method of claim 1 further comprising the step of conducting a frequency sweep for measuring the resonant frequency and the anti-resonant frequency.

3. The method of claim 1 wherein the phase margin and the output displacement are correlated according to an equation stored in a generator console for the hand piece.

4. The method of claim 1 wherein the phase margin and the output displacement are correlated according to an equation stored in a test equipment for the hand piece during manufacture.

5. The method of claim 1 wherein the correlating step is implemented by accessing a memory with tabulated data on the phase margin and the drive current.

6. The method of claim 5 wherein the tabulated data are stored in a test equipment for the hand piece during manufacture.

7. The method of claim 5 wherein the tabulated data are stored in a generator console for the hand piece.

8. The method of claim 1 further comprising a calibration step, the calibration step comprises the sub-steps of:
    (a) measuring a resonant frequency for calibration;
    (b) measuring an anti-resonant frequency for calibration;
    (c) calculating a phase margin for calibration which is the difference of the resonant frequency for calibration and the anti-resonant frequency for calibration; and
    (d) correlating the phase margin for calibration with an output displacement for calibration.

9. The method of claim 8 wherein the substeps (a), (b), (c) and (d) are implemented by a generator console for the hand piece.

10. The method of claim 8 wherein the output displacement is generally equal to 38.156 minus 0.0751 multiplied by the phase margin.

11. The method of claim 1 further comprising the step of storing the drive current in the hand piece.

12. A system for operating an ultrasonic surgical hand piece comprising:
    means for measuring a resonant frequency of the hand piece;
    means for measuring an anti-resonant frequency of the hand piece;
    means for calculating a phase margin which is the difference of the resonant frequency and the anti-resonant frequency;
    means for correlating the phase margin with an output displacement;
    means for calculating a drive current based on the correlation of the phase margin with the output displacement; and
    means for driving the hand piece with the drive current.

13. The system of claim 12 further comprising means for conducting a frequency sweep for measuring the resonant frequency and the anti-resonant frequency.

14. The system of claim 12 further comprising a generator console for the hand piece wherein the phase margin and the output displacement are correlated according to an equation stored in the generator console.

15. The system of claim 12 wherein the phase margin and the output displacement are correlated during manufacture according to a stored equation for the hand piece.

16. The system of claim 12 wherein the correlating is implemented by accessing a memory with tabulated data on the phase margin and the drive current.

17. The system of claim 16 wherein the tabulated data are stored in a test equipment for the hand piece during manufacture.

18. The system of claim 16 wherein the tabulated data are stored in a generator console for the hand piece.

19. The system of claim 12 wherein the output displacement is generally equal to 38.156 minus 0.0751 multiplied by the phase margin.

20. A method for operating an ultrasonic surgical hand piece with a transducer, the method comprising the steps of:
    running the transducer at resonance;
    measuring a drive current of the hand piece;
    measuring an output displacement of the hand piece;
    inputting a desired output displacement;
    calculating a desired drive current which about equals the desired output displacement multiplied by the measured drive current divided by the measured output displacement; and
    driving the hand piece with the desired drive current.

* * * * *